(12) United States Patent
Ramamoorthy et al.

(10) Patent No.: US 11,092,605 B2
(45) Date of Patent: Aug. 17, 2021

(54) POLYMER-BASED LIPID NANODISCS AND MACRODISCS

(71) Applicant: THE REGENTS OF THE UNIVERSITY OF MICHIGAN, Ann Arbor, MI (US)

(72) Inventors: Ayyalusamy Ramamoorthy, Ann Arbor, MI (US); Thirupathi Ravula, Ann Arbor, MI (US); Nathaniel Z. Hardin, Ann Arbor, MI (US); Sarah J. Cox, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/198,397

(22) Filed: Nov. 21, 2018

(65) Prior Publication Data

US 2019/0154698 A1  May 23, 2019

Related U.S. Application Data

(60) Provisional application No. 62/589,865, filed on Nov. 22, 2017.

(51) Int. Cl.
*G01N 33/68* (2006.01)
*B01J 13/08* (2006.01)
(Continued)

(52) U.S. Cl.
CPC .......... *G01N 33/6842* (2013.01); *B01J 13/08* (2013.01); *C08F 8/12* (2013.01); *C08F 8/32* (2013.01); *C08F 8/44* (2013.01); *C08F 8/48* (2013.01); *C08F 212/08* (2013.01); *G01N 21/35* (2013.01); *C08F 2800/10* (2013.01);
(Continued)

(58) Field of Classification Search
None
See application file for complete search history.

(56) References Cited

U.S. PATENT DOCUMENTS 8,623,414 B2   1/2014  Tonge
2010/0062067 A1   3/2010  Tonge et al.

OTHER PUBLICATIONS

Fiori MC, Polymer-encased nanodiscs with improved buffer compatibility, Aug. 7, 2017, Scientific Reports, 7, 7432 (Year: 2017).*
(Continued)

*Primary Examiner* — Celeste A Roney
(74) *Attorney, Agent, or Firm* — Marshall, Gerstein & Borun LLP

(57) ABSTRACT

The disclosure provides a lipid nanodisc including a lipid bilayer having two opposing hydrophilic faces and a hydrophobic edge between the hydrophilic faces, and a copolymer encircling the hydrophobic edge of the lipid bilayer, the copolymer including a first monomeric unit including a pendant aromatic group, and a second monomeric unit including a pendant hydrophilic group, wherein the first monomeric unit and the second monomeric unit are present in the copolymer is a molar ratio ranging from 1:1 to 3:1 for the first monomeric unit:the second monomeric unit. The disclosure further provides a method of making the polymer-based lipid nanodiscs of the disclosure and methods of characterizing membrane proteins using the polymer-based lipid nanodiscs of the disclosure.

23 Claims, 5 Drawing Sheets

(51) Int. Cl.
| | |
|---|---|
| C08F 212/08 | (2006.01) |
| G01N 21/35 | (2014.01) |
| C08F 8/48 | (2006.01) |
| C08F 8/44 | (2006.01) |
| C08F 8/12 | (2006.01) |
| C08F 8/32 | (2006.01) |
| G01N 24/08 | (2006.01) |

(52) U.S. Cl.
CPC ........ C08F 2810/50 (2013.01); G01N 24/088 (2013.01); G01N 2021/3595 (2013.01); G01N 2405/00 (2013.01); G01N 2570/00 (2013.01)

(56) References Cited

OTHER PUBLICATIONS

MSDS, (2-aminoethyl)trimethylammonium, Oct. 8, 2009 (Year: 2009).*
Ravula et al (Agnew Chem Int Ed, 2017, 56, 11466-11470). (Year: 2017).*
Ahuja et al., A model of the membrane-bound cytochrome b5-cytochrome P450 complex from NMR and mutagenesis data, J. Biol. Chem., 288(30):22080-95 (Jul. 2013).
Almgren, Mixed micelles and other structures in the solubilization of bilayer lipid membranes by surfactants, Biochim. Biophys. Acta, 1508(1-2):146-63 (Nov. 2000).
Bayburt et al., Assembly of single bacteriorhodopsin trimers in bilayer nanodiscs, Arch. Biochem. Biophys., 450(2):215-22 (Jun. 2006).
Bennett et al., Chemical shift correlation spectroscopy in rotating solids: Radio frequency-driven dipolar recoupling and longitudinal exchange, J. Chem. Phys., 96:8624 (1992).
Denisov et al., Nanodiscs for structural and functional studies of membrane proteins, Nat. Struct. Mol. Biol., 23(6):481-6 (Jun. 2016).
Drews, Drug discovery: a historical perspective, Science, 287(5460):1960-4 (Mar. 2000).
Dvinskikh et al., A high-resolution solid-state NMR approach for the structural studies of bicelles, J. Am. Chem. Soc., 128(19):6326-7 (May 2006).
Dvinskikh et al., High-resolution 2D NMR spectroscopy of bicelles to measure the membrane interaction of ligands, J. Am. Chem. Soc., 129(4):794-802 (Jan. 2007).
Dvinskikh et al., Sensitivity and resolution enhancement in solid-state NMR spectroscopy of bicelles, J. Magn. Reson., 184:228-35 (2007).
Dörr et al., Detergent-free isolation, characterization, and functional reconstitution of a tetrameric K+ channel: the power of native nanodiscs, Proc. Natl. Acad. Sci. USA, 111(52):18607-12 (Dec. 2014).
Dörr et al., The styrene-maleic acid copolymer: a versatile tool in membrane research, Eur. Biophys. J., 45(1):3-21 (Jan. 2016).
Hagn et al., Optimized phospholipid bilayer nanodiscs facilitate high-resolution structure determination of membrane proteins, J. Am. Chem. Soc., 135(5):1919-25 (Feb. 2013).
Hester et al., Separated Local Field Spectra in NMR: Determination of Structure of Solids, Phys. Rev. Lett., 36(18):1081-3 (1976).
Kondo et al., Formation of size-controlled, denaturation-resistant lipid nanodiscs by an amphiphilic self-polymerizing peptide, Colloids Surf. B Biointerfaces, 146:423-30 (Oct. 2016).
Lee et al., A method for detergent-free isolation of membrane proteins in their local lipid environment, Nat. Protoc., 11(7):1149-62 (Jul. 2016).
Li et al., Structural analysis of nanoscale self-assembled discoidal lipid bilayers by solid-state NMR spectroscopy, Biophys. J., 91(10):3819-28 (Nov. 2006).
Marassi et al., A Solid-State NMR Index of Helical Membrane Protein Structure and Topology, J. Magnetic Resonance, 144(1):150-5 (May 2000).
Murray et al., Membrane protein structural validation by oriented sample solid-state NMR: diacylglycerol kinase, Biophys. J., 106(8):1559-69 (Apr. 2014).
Opella et al., Structure determination of membrane proteins by NMR spectroscopy, Biochem. Cell Biol., 80(5):597-604 (2000).
Orwick et al., Detergent-free formation and physicochemical characterization of nanosized lipid-polymer complexes: Lipodisq, Angew. Chem. Int. Ed. Engl., 51(19):4653-7 (May 2012).
Orwick-Rydmark et al., Detergent-free incorporation of a seven-transmembrane receptor protein into nanosized bilayer Lipodisq particles for functional and biophysical studies, Nano Lett., 12(9):4687-92 (Sep. 2012).
Ramamoorthy et al., Experimental Aspects of Multidimensional Solid-State NMR Correlation Spectroscopy, J. Magnetic Resonance, 140(1):131-40 (Sep. 1999).
Ramamoorthy et al., PISEMA Solid-State NMR Spectroscopy, Ann. Reports on NMR Spectroscopy, 52:1-52 (2004).
Ravula et al., pH tunable divalent metal ion tolerant polymer lipid nanodiscs, Langmuir, 33 (40), pp. 10655-10662 (2017).
Ritchie et al., Chapter 11—Reconstitution of membrane proteins in phospholipid bilayer nanodiscs, Methods Enzymol., 464:211-31 (2009).
Rothgeb et al., Nitrogen-14 nuclear magnetic resonance spectroscopy as a probe of lipid bilayer headgroup structure, J. Biol. Chem., 256(12):6004-9 (Jun. 1981).
Santos et al., Effects of antidepressants on the conformation of phospholipid headgroups studied by solid state NMR, Magn. Reson. Chem., 42:105-14 (2004).
Schiedelaar et al., Molecular model for the solubilization of membranes into nanodisks by styrene maleic Acid copolymers, Biophys J., 108(2):279-90 (Jan. 2015).
Semchyschyn et al., Conformational response of the phosphatidylcholine headgroup to bilayer surface charge: torsion angle constraints from dipolar and quadrupolar couplings in bicelles, Magn. Reson. Chem.,, 42:89-104 (2004).
Thiriot et al., Structure of the coat protein in Pf1 bacteriophage determined by solid-state NMR spectroscopy, J. Mol. Biol., 341(3):869-79 (Aug. 2004).
Vosegaard et al., Helix conformations in 7TM membrane proteins determined using oriented-sample solid-state NMR with multiple residue-specific 15N labeling, Biophys. J., 94(1):241-50 (Jan. 2008).
Zhang et al., Reconstitution of the Cytb5-CytP450 Complex in Nanodiscs for Structural Studies using NMR Spectroscopy, Angew. Chem. Int. Ed. Engl., 55(14):4497-9 (Mar. 2016).
Ravula et al., Formation of pH-resistant monodispersed polymer-lipid nanodiscs, Angew. Chem. Int. Ed., 57:1342-5 (2018).
Ravula et al., Bioinspired, size-tunable self-assembly of polymer-lipid bilayer nanodiscs, Angew. Chem. Int. Ed., 56:11466-70 (2017).
Knowles et al., Membrane proteins solubilized intact in lipid containing nanoparticles bounded by styrene maleic acid copolymer, J. Am. Chem. Soc., 131:7484-5 (2009).
Lindhoud et al., SMA-SH: Modified styrene-maleic acid copolymer for functionalization of lipid nanodiscs, Biomacromolecules, 17:1516-22 (2016).

* cited by examiner

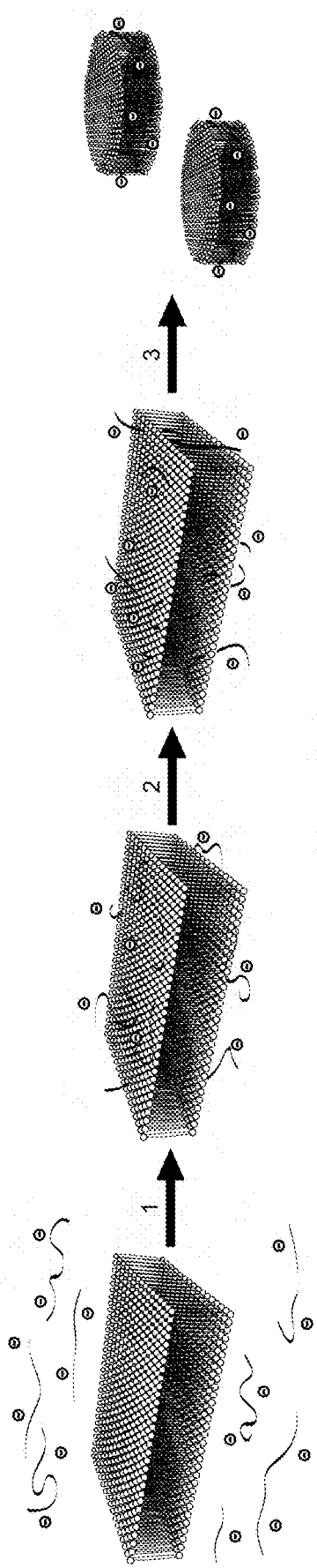
Figure 1
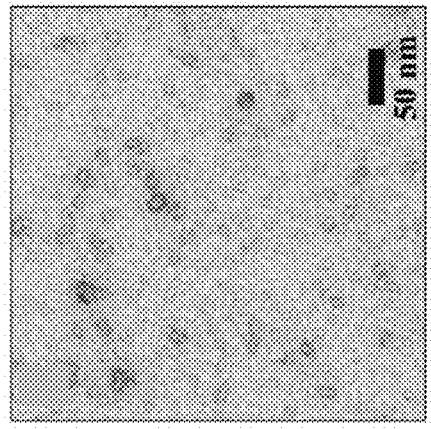
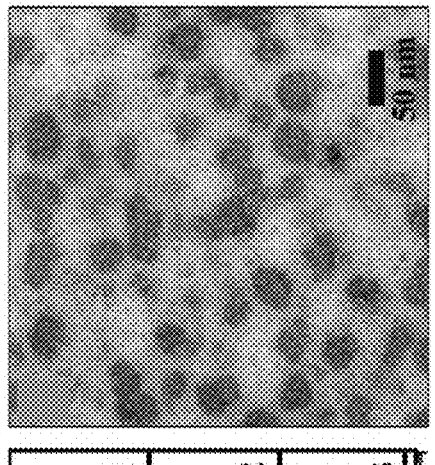
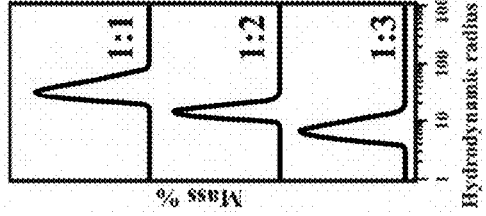
Figure 2A　　Figure 2B　　Figure 2C

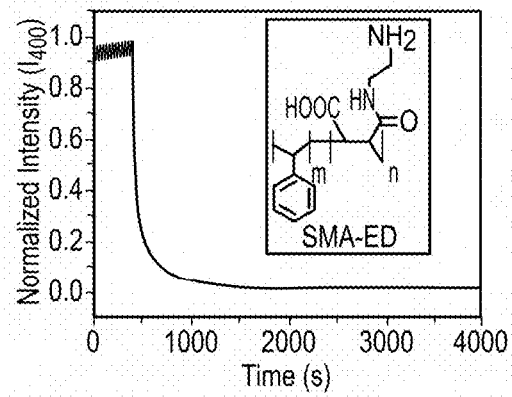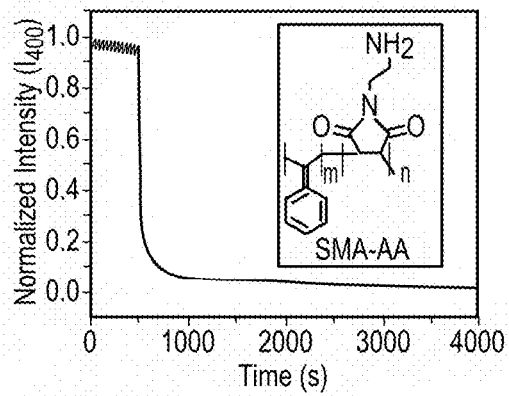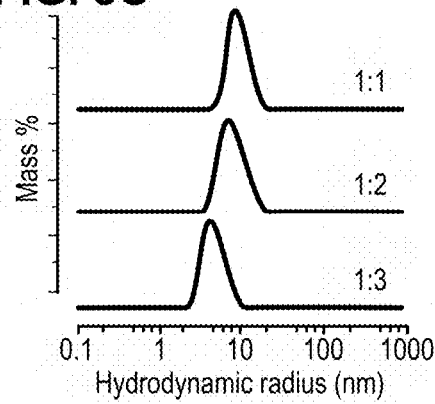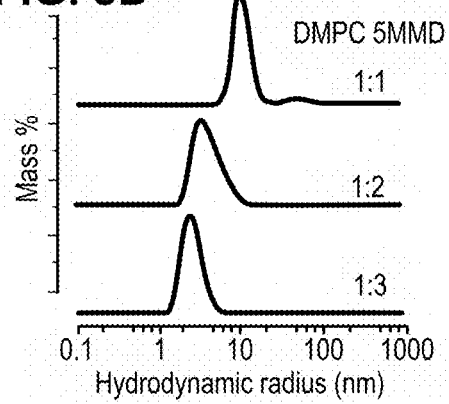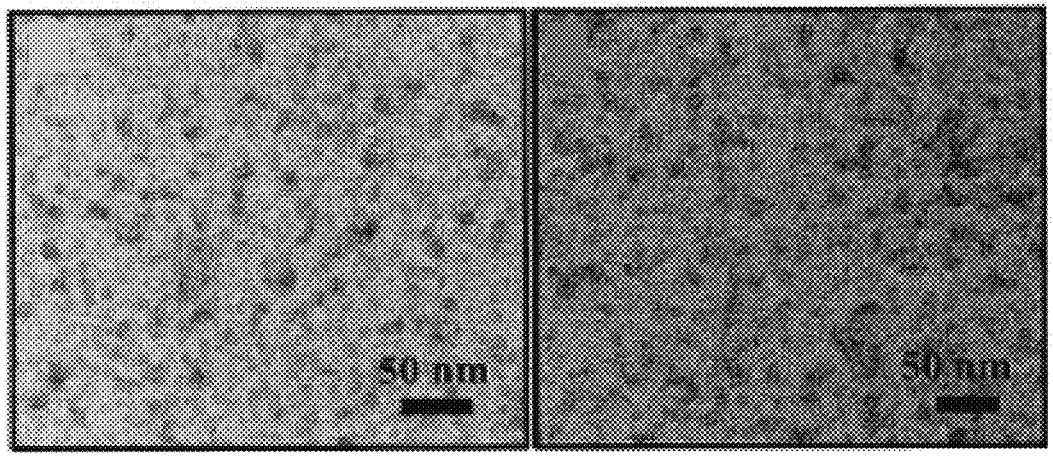

POLYMER-BASED LIPID NANODISCS AND MACRODISCS

STATEMENT OF GOVERNMENT SUPPORT

This invention was made with government support under grant numbers GM084018 and AG048934 awarded by the National Institutes of Health. The government has certain rights in the invention.

FIELD OF THE DISCLOSURE

The disclosure relates generally to lipid nanodiscs. In particular, the disclosure relates to polymer-based lipid nanodiscs.

BACKGROUND

Determination of the structure and function of membrane proteins is a challenge due to the difficulty of developing methods of extracting membrane proteins from their native environment, while preserving the correct conformation of the protein in isolation from its native environment. Traditional protocols involve extracting membrane proteins from their native environment using detergents and then including the proteins in a model bilayer system. Unfortunately, the use of detergents leads to issues such as protein inactivation and sample aggregation.

In order to avoid the use of detergents, methods for the isolation, purification, and characterization of membrane proteins have been developed which reconstitute membrane proteins in nanodiscs. Nanodiscs are disc-shaped patches of lipid bilayers surrounded by an amphiphilic belt. Amphiphilic belts that have been used in preparing nanodiscs include different sized membrane scaffold proteins, peptides, and polymers. Membrane scaffold protein-based nanodiscs are good mimics of the membrane; however, the reconstitution of the membrane proteins still require the use of detergents. Additionally, protein-based nanodiscs are restricted to a narrow range of size, difficult to prepare, and expensive to produce. Peptide-based nanodiscs are also limited by several disadvantages, including stability issues, interference from the peptides in biophysical measurements, and are expensive to produce. Similarly, polymer-based nanodiscs are limited by disadvantages including restricted size range, their non-tolerance in the presence of divalent metal ions and different pH, and are expensive to produce. Thus, a need exists for nanodiscs that can address these difficulties.

SUMMARY

One aspect of the disclosure provides a lipid nanodisc including a lipid bilayer having two opposing hydrophilic faces and a hydrophobic edge between the hydrophilic faces, and a copolymer encircling the hydrophobic edge of the lipid bilayer, the copolymer including a first monomeric unit including a pendant aromatic group and/or a pendant alkyl group (e.g., only pendant (hydrophobic) aromatic groups, only pendant (hydrophobic) alkyl groups, or both pendant (hydrophobic) aromatic groups and pendant (hydrophobic) alkyl groups), and a second monomeric unit including a pendant hydrophilic group, wherein the first monomeric unit and the second monomeric unit are present in the copolymer in a molar ratio ranging from 1:1 to 3:1 for the first monomeric unit:the second monomeric unit.

Another aspect of the disclosure provides a method of making a lipid nanodisc, the method including contacting a lipid and a copolymer including a first monomeric unit including a pendant aromatic group, and a second monomeric unit including a pendant hydrophilic group, wherein the first monomeric unit and the second monomeric unit are present in the copolymer is a molar ratio ranging from 1:1 to 3:1 for the first monomeric unit:the second monomeric unit, to form a lipid nanodisc including a lipid bilayer having two opposing hydrophilic faces and a hydrophobic edge between the hydrophilic faces and the copolymer encircling the hydrophobic edge of the lipid bilayer.

Another aspect of the disclosure provides a lipid nanodisc, including a lipid bilayer having two opposing hydrophilic faces and a hydrophobic edge between the hydrophilic faces, and a styrene/modified maleic anhydride copolymer encircling the hydrophobic edge of the lipid bilayer, the copolymer having a pendant hydrophilic group and a styrene to maleic anhydride molar ratio of about 1.1:1 to 1.5:1.

Another aspect of the disclosure provides a method of making a lipid nanodisc, the method including contacting a lipid and a styrene/modified maleic anhydride copolymer having a pendant hydrophilic group and a styrene to maleic anhydride molar ratio of about 1.1:1 to 1.5:1, to form a lipid nanodisc including a lipid bilayer having two opposing hydrophilic faces and a hydrophobic edge between the hydrophilic faces and the copolymer encircling the hydrophobic edge of the lipid bilayer.

Another aspect of the disclosure provides a method of characterizing a membrane protein, the method including contacting a lipid nanodisc of the disclosure with a membrane protein to form a membrane protein-nanodisc including the membrane protein spanning across the lipid bilayer from the first hydrophilic face to the second hydrophilic face, and characterizing the lipid nanodisc including the membrane protein.

Further aspects and advantages will be apparent to those of ordinary skill in the art from a review of the following detailed descriptions. While the compositions and methods are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the present invention, two drawing figures are attached hereto.

FIG. 1 shows a simplified schematic representation of nanodisc formation.

FIG. 2 shows the difference in maximum lipid nanodisc size obtained using different lipid:copolymer weight ratios.

FIG. 3 shows the difference in maximum lipid nanodisc size obtained using different lipid:copolymer weight ratios for SMA-ED and SMAd-A copolymers.

DETAILED DESCRIPTION

Figure 4A:
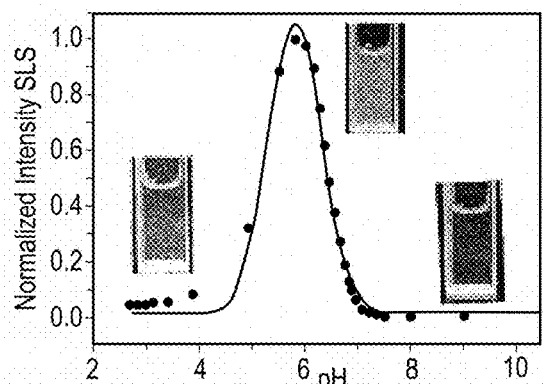
FIG. 4 shows the stability of polymer nanodiscs versus pH for SMA-ED polymers and SMAd-A polymers.
Figure 4B:
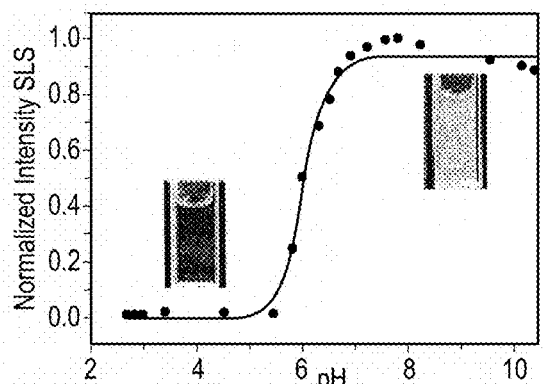

Provided herein are polymer-based lipid nanodiscs and methods of making and using same. In general, the polymer-based lipid nanodiscs disclosed herein include a copolymer having a first monomeric unit including a pendant aromatic group, and a second monomeric unit including a pendant hydrophilic group, wherein the first monomeric unit and the second monomeric unit are present in the copolymer is a molar ratio ranging from 1:1 to 3:1 for the first monomeric unit:the second monomeric unit. The copolymers described herein provide one or more advantages, for example, extracting membrane proteins without the use of detergents, forming nanodiscs with native lipid bilayers, solubilization of lipid bilayers, forming nanodiscs over wide pH ranges, and forming nanodiscs over a wide range of sizes. Additionally, the copolymer is stable for periods of at least 6 months, can be stored as a powder, and does not require purification by high performance liquid chromatography (HPLC).

In contrast to the copolymers according to the disclosure, when styrene/maleic acid copolymers having a styrene:maleic acid molar ratio of 2:1 or 3:1 and a molecular weight in the range of 7.5 to 10 kDa were used to form nanodiscs, only the higher molecular weight polymers formed nanodiscs and the resulting nanodiscs had narrow diameter ranges of about 5 to about 15 nm.

Copolymer

The copolymer of the disclosure can include a first monomeric unit including a hydrophobic pendant aromatic group and a second monomeric unit including a pendant hydrophilic group. The copolymer of the disclosure can include a first monomeric unit including a hydrophobic pendant alkyl group and a second monomeric unit including a pendant hydrophilic group. In some embodiments, the copolymer can be a random copolymer or an alternating copolymer. Without intending to be bound by theory, it is believed that the hydrophobic pendant aromatic group and/or hydrophobic pendant alkyl group inserts into the hydrophobic portion of a lipid bilayer and the hydrophilic group interacts with an aqueous medium and the hydrophilic portion of the lipid bilayer to spontaneously form lipid nanodiscs. A simplified schematic representation of the formation of lipid nanodiscs is shown in FIG. 1, wherein step 1 involves the electrostatic interaction of the copolymer with the surface of the lipid bilayer, step 2 involves the hydrophobic aromatic fraction of the polymer chains embedding into the bilayer, and step 3 involves the spontaneous formation of nanodiscs.

Suitable hydrophobic pendant aromatic groups include, but are not limited to substituted and unsubstituted benzene and naphthalene. The first monomeric units including a hydrophobic aromatic group can be derived from substituted or unsubstituted vinyl aromatic monomers, including but not limited to vinyl benzenes (e.g., styrene, vinyl toluene, vinyl xylenes), vinyl naphthalenes, vinyl anthracene, and vinyl phenanthrene. In some embodiments, the vinyl aromatic monomer can include a vinyl functional group tethered to the pendant aromatic group via a $C_1$-$C_{10}$ or $C_1$-$C_6$ alkylene linking group. In some embodiment, the pendant aromatic group can be substituted with one or more alkyl groups (e.g., $C_1$-$C_3$ alkyl groups) on the aromatic ring and/or substituted with one or more heteroatoms (e.g., N, O, S heteroatoms) within the aromatic ring. In some embodiments, the hydrophobic pendant aromatic group is planar. Without intending to be bound by theory, it is believed that the planar nature of the aromatic can facilitate the insertion of the aromatic group into the hydrophobic portion of the lipid bilayer. In some cases, the first monomeric unit includes a styrene monomer unit.

The first monomeric unit can also include a hydrophobic pendant alkyl group. As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

In embodiments, the hydrophobic pendant alkyl groups comprise $C_1$-$C_7$ n-alkyl groups and/or $C_3$-$C_{10}$ branched alkyl groups. Suitable hydrophobic pendant alkyl groups include, but are not limited to, methyl, ethyl, n-propyl, i-propyl, n-butyl, i-butyl, s-butyl and t-butyl. The first monomeric units including a hydrophobic alkyl group can be derived from substituted or unsubstituted vinyl alkyl monomers, including, but not limited to, propylene, α-butylene (1-butene), 1-pentene, 3-methyl-1-butene (isopentene), 1-hexene, 4-methyl-1-pentene, 3-methyl-1-pentene, 2-methyl-1-pentene, 3,3-dimethyl-1-butene, and 2,3-dimethyl-1-butene.

The second monomeric unit including a pendant hydrophilic group and can optionally further include at least one of a pendant carboxylic acid group and a carboxylate group. Suitable second monomeric units can be derived from vinyl monocarboxylic acids or their esters, dicarboxylic monomers having a polymerizable double bond, their esters or anhydrides, and alkali metal salts of any of the foregoing. Examples of suitable monomer units include vinyl acetic acid, maleic acid, monoalkyl maleate, dialkyl maleate, maleic anhydride, fumaric acid, monoalkyl fumarate dialkyl fumarate, itaconic acid, monoalkyl itaconate, dialkyl itaconate, itaconic anhydride, citraconic acid, monoalkyl citraconate, dialkyl citraconate, citraconic anhydride, mesaconic acid, monoalkyl mesaconate, dialkyl mesaconate, glutaconic acid, monoalkyl glutaconate, dialkyl glutaconate, glutaconic anhydride, alkyl acrylates, alkyl alkacrylates, alkali metal salts of the foregoing, esters of the foregoing, and combinations of the foregoing. In some cases, the second monomeric unit includes a modified maleic anhydride or modified maleic acid monomer unit. In some cases, the second monomeric unit includes an alkanolamine-modified acid or alkanolamine-modified anhydride. In some cases, the second monomer unit includes an alkylenediamine-modified acid or alkylenediamine-modified anhydride. In some cases, the second monomer unit includes an (aminoalkyl)trialkylammonium modified acid or (aminoalkyl)trialkylammonium modified anhydride.

As used herein, and unless specified otherwise, "alkanolamine-modified acid (or anhydride)" means an amide reaction product between an alkanolamine and a carboxylic acid (or corresponding anhydride). As used herein, and unless specified otherwise, "alkylenediamine-modified acid (or anhydride)" means an amide reaction product between an alkylenediamine and a carboxylic acid (or corresponding anhydride). As used herein, and unless specified otherwise, "(aminoalkyl)trialkylammonium modified acid (or anhydride)" means an amide reaction product between and (aminoalkyl)trialkylammonium and a carboxylic acid (or corresponding anhydride).

The pendant hydrophilic group can include any hydrophilic group suitable to solubilize the lipid nanodisc in an aqueous solution. For example, the pendant hydrophilic group can include at least one of hydroxyl, amino, carboxylic acid, carboxylate, phosphate, phosphonate, carboxylic ether, carboxylic ester, phosphate ester, amide, phosphonamide, or salts of the foregoing. The pendant hydrophilic group can be a fluorescent group or can further include a fluorescent group. The monomer comprising the pendant hydrophilic group can be neutral, positively charged, negatively charged, or zwitterionic. In embodiments, the pendant hydrophilic group can be neutral, positively charged or negatively charged. Positively charged hydrophilic groups can include, but are not limited to, ammonium cations (e.g., alkylammonium cations, such as mono-, di-, tri-, or tetra-alkyl ammonium cations). Negatively charged hydrophilic groups can include, but are not limited to, carboxylate or phosphate. The pendant hydrophilic group can be a chelating group or can further include a chelating group. The chelating group can further include a metal ion bound thereto. A pendant hydrophilic group including a fluorescent group or chelating group having a metal ion bound thereto can advantageously provide a spectroscopic tag to provide additional characterization of the lipid nanodiscs including the copolymers of the disclosure. Suitable fluorescent tags can include, but are not limited to, cyanine5 amine and Alexa fluor 488. Suitable metal chelating tags include, but are not limited to, ethylenediaminetetraacetic acid (EDTA) and lanthanide binding tags.

The hydrophilic group can be linked to the second monomeric unit via an amide, ester, or glycosidic bond, for example. The hydrophilic group can be linked to the second monomeric unit by the reaction of a carboxylic group or corresponding anhydride of the second monomer unit and a nucleophilic group provided on the pendant hydrophilic group, for example, an amino or hydroxyl group. In some cases, the pendant hydrophilic group includes an amide reaction product of a carboxylic group of the second monomer unit and an amine compound including at least one of an alkanolamine, an alkylenediamine, and an amino acid. In some cases, the pendant hydrophilic group includes an amide reaction product of maleic anhydride and an amine compound including at least one of an alkanolamine, an alkyldiamine, and an amino acid.

The hydrophilic pendant group can further include an alkyl group, for example as a spacer or linker between the hydrophilic group and the polymer backbone. The length of the alkyl group is not particularly limiting. Thus, the hydrophilic group can be separated from the copolymer backbone by an alkyl group larger than a $C_{10}$ alkyl group, a $C_1$-$C_{10}$ alkyl group, or a $C_{1-6}$ alkyl group, for example. In some cases, the pendant hydrophilic group can include a $C_1$-$C_6$ alkyl group including a terminal hydrophilic group. In some cases, the pendant hydrophilic group can include a $C_{1-6}$ alkyl group including a terminal hydrophilic group selected from hydroxyl, amino, carboxylic acid, carboxylate, phosphate, phosphonate, carboxylic ether, carboxylic ester, phosphate ester, amide, phosphonamide, ammonium, or salts of the foregoing.

In some cases, the hydrophilic group includes an ethylhydroxy group. In some cases, the copolymer includes an alkanolamine modified styrene/maleic anhydride copolymer. In some cases, the copolymer includes an ethanolamine modified styrene/maleic anhydride copolymer.

In some cases, the hydrophilic group includes an ethylenediamine group. In some cases, the copolymer includes an alkylenediamine modified styrene/maleic anhydride copolymer. In some cases, the copolymer includes an ethylenediamine modified styrene/maleic anhydride copolymer.

The pendant hydrophilic group can be provided in any amount suitable to aid in solubilization of the lipid nanodisc. For example, when the second monomeric unit includes a monocarboxylic acid or ester, each carboxyl group can be modified (i.e., a pendant hydrophilic group to second monomer unit molar ratio of 1:1), or only some of the carboxyl groups can be modified to include the pendant hydrophilic group (e.g., 10 percent of the carboxyl groups may be modified to provide a pendant hydrophilic group to second monomer unit molar ratio of 1:10). Thus, the pendant hydrophilic group to second monomer unit molar ratio can be in a range of about 1:1 to about 1:10, for example, about 1:1 to about 1:4, or about 1:1 to about 1:3, or about 1:1 to about 1:2, for example, about 1:1. Further, when the second monomeric unit includes a dicarboxylic acid, ester, or anhydride, each carboxyl group can be modified (i.e., a pendant hydrophilic group to second monomer unit molar ratio of 2:1), or only some of the carboxyl groups can be modified to include the pendant hydrophilic group (e.g., a pendant hydrophilic to second monomer unit molar ratio of about 1:10). In some embodiments, one carboxyl group of each monomeric unit including a dicarboxylic group can be modified to include the pendant hydrophilic group (e.g., a pendant hydrophilic group to second monomer unit molar ratio of 1:1). Thus, the pendant hydrophilic group to second monomer unit molar ratio can be in a range of about 2:1 to about 1:10, for example, about 2:1 to about 1:4, or about 2:1 to about 1:3, or about 2:1 to about 1:2, or about 1:1. Methods of modifying carboxyl groups to include pendant hydrophilic groups are well known in the art. For example, when the copolymer including a carboxyl group is an anhydride, the anhydride can be treated with an alkanolamine in the presence of N,N-dimethylmethanamine, followed by hydrolysis of any unreacted anhydride, if necessary, to provide a pendant hydroxyl group bound to the copolymer through an amide linkage.

The first monomeric unit to the second monomeric unit can be present in the copolymer in a molar ratio ranging from about 1:1 to about 3:1 for the first monomeric unit:the second monomeric unit. For example, the molar ratio of the first monomeric unit to the second monomeric unit can be in a range of about 1:1 to about 3:1, about 1:1 to about 2:1, about 1.1:1 to about 1.8:1, about 1.1:1 to about 1.5:1, for example, about 1.1:1, about 1.2:1, about 1.3:1, about 1.4:1, or about 1.5:1. In some cases, the copolymer includes a styrene/modified maleic anhydride copolymer having a styrene to maleic anhydride molar ratio of about 1.3:1. Without intending to be bound by theory, it is believed that the ability of a polymer to form a lipid nanodisc depends on the ratio of hydrophobic:hydrophilic monomer units, for a given polymer molecular weight.

The copolymer can have a number-average molecular weight in a range of about 1 kDa to about 6 kDa, for example, about 1 kDa to about 5 kDa, about 1 kDa to about 3 kDa, or about 1 kDa to about 2 kDa, for example, about 1 kDa, about 1.2 kDa, about 1.3 kDa, about 1.4 kDa, about 1.5 kDa, about 1.6 kDa, about 1.7 kDa, about 1.8 kDa, about 1.9 kDa, or about 2 kDa. Without intending to be bound by theory, it is believed that the use of a low molecular weight polymer allows for the rearrangement of the polymer hydrophobic units within the lipid bilayer, resulting in flexibility of the resulting nanodisc amphiphilic belt. In contrast, it is believed that high molecular weight polymers have more restricted movement within and among the lipid bilayer. Accordingly, it is believed that because of the ability of the lower molecular weight polymers to rearrange, the size of the lipid nanodiscs prepared using a low molecular weight polymer can vary over a wide range of sizes, depending on the ratio of lipid:polymer used to prepare the nanodiscs.

When in solution (e.g., during preparation of the nanodiscs), the copolymer can include monomer units that are neutral, positively charged, negatively charged, or zwitterionic, depending on the pH of the solution.

Lipid Nanodiscs

The polymer-based lipid nanodiscs disclosed herein further include a lipid. The lipid is not particularly limited. The lipid can include a natural cell membrane extract. Suitable lipids include, but are not limited to phosphatidylethanolamines, phosphatidylcholines, phosphatidylglycerols, phosphatidylserines, cholesterols, sphingomyelin, gangliosides, lipopolysaccharides, phophatidylinositols, and derivatives of the foregoing. In some cases, the lipid comprises at least one of phosphatidylethanolamines, phosphatidylcholines, phosphatidylglycerols, phosphatidylserines, cholesterols, sphingomyelin, gangliosides, lipopolysaccharides, and phophatidylinositols. In some cases, the lipid is a phospholipid. In some cases, the phospholipid includes a phosphatidylcholine.

The lipid in the nanodisc forms a lipid bilayer including two opposing hydrophilic faces, and a hydrophobic edge between the hydrophilic faces. The hydrophobic edge is made up of the hydrophobic tails from both layers of the lipid bilayer. The center of the hydrophobic edge is the point at which the hydrophobic tail from one layer of the bilayer meets the hydrophobic tail from the second layer of the bilayer. The nanodisc further includes a copolymer of the disclosure encircling the hydrophobic edge of the lipid bilayer.

In some embodiments, the lipid includes a phosphatidylcholine, the copolymer includes a styrene/maleic anhydride copolymer modified with an ethanolamine, the styrene/maleic anhydride copolymer has a styrene to maleic anhydride ratio in a range of about 1.1:1 to about 1.5:1 and a molecular weight in a range of about 1 kDa to about 3 kDa.

The lipid nanodiscs of the disclosure can have a diameter in a range of about 6 nm to about 100 nm, for example, about 6 nm to about 100 nm, about 10 nm to about 90 nm, about 20 nm to about 90 nm, about 30 nm to about 80 nm, about 40 nm to about 80 nm, about 50 nm to about 70 nm, or about 55 nm to about 65 nm. In some cases, the nanodisc has a diameter less than or equal to 40 nm, for example, in a range of about 6 nm to 40 nm, about 10 nm to about 35 nm, about 20 nm to about 35 nm, or about 25 nm to about 30 nm. In some cases, the nanodisc has a diameter greater than 40 nm, for example, 41 nm to about 100 nm, about 45 nm to about 90 nm, about 50 nm to about 80 nm, about 50 nm to about 70 nm, or about 60 nm. Nanodiscs having a diameter greater than 40 nm may be referred to as "macrodiscs." The size of the nanodisc can be controlled by changing the lipid:copolymer weight ratio during preparation. In general, as the amount of copolymer increases relative to the amount of lipid, the size of the resulting nanodisc decreases. Similarly, as the amount of copolymer decreases relative to the amount of lipid, the size of the resulting nanodisc increases.

In some cases, the lipid nanodisc can be characterized in that when a magnetic field is applied, the nanodisc aligns with the magnetic field. Such a characteristic can be advantageous, for example, when characterizing the nanodisc (or a membrane protein provided therein) by NMR spectroscopy.

The lipid nanodisc can further include a membrane protein. The membrane protein can be any protein that interacts with or is part of a biological membrane, and can be permanently anchored or temporarily anchored to a lipid bilayer. Suitable membrane proteins include, but are not limited to U-$^{15}$N Cytb5, cytochomromes such as cytochrome b5, cytochrome P450, cytochrome P450 reductase, and cytochrome c, outer membrane proteins, and G-protein-coupled receptors (GPCRs). When a membrane protein is included in the lipid nanodisc, the membrane protein spans across at least one half of the lipid bilayer, from one hydrophilic face to the center of the hydrophobic edge. In some cases, the membrane protein spans across the entire lipid bilayer from the first hydrophilic face to the second hydrophilic face at least once. In some cases, the membrane protein spans across the entire lipid bilayer from the first hydrophilic face to the second hydrophilic face more than once.

Method of Preparing Lipid Nanodisc

Further provided herein are methods of making a lipid nanodisc, the method including contacting a lipid and a copolymer including a first monomeric unit including a pendant aromatic group, and a second monomeric unit including a pendant hydrophilic group, wherein the first monomeric unit and the second monomeric unit are present in the copolymer is a molar ratio ranging from 1:1 to 3:1 for the first monomeric unit:the second monomeric unit, to form a lipid nanodisc including a lipid bilayer having two opposing hydrophilic faces and a hydrophobic edge between the hydrophilic faces and the copolymer encircling the hydrophobic edge of the lipid bilayer. In some cases, the copolymer includes a styrene/modified maleic anhydride copolymer having a styrene to maleic anhydride molar ratio of about 1.1:1 to 1.5:1, the copolymer including a pendant hydrophilic group. Advantageously the nanodiscs of the disclosure are easy to prepare, inexpensive and stable for up to about a month.

The lipid and copolymer can be any lipid and copolymer described herein. The method of preparing the lipid nanodisc includes contacting the lipid and the copolymer. In some cases the lipid is provided as a multilamellar vesicle. Without intending to be bound by theory, it is believed that when the lipid is provided as a multilamellar vesicle, the polymer chains get inserted into the lipid bilayer and break the multilamellar vesicle into nanodisc-shaped lipoparticles. The lipid can include a natural cell membrane extract.

The lipid can further include a membrane protein such that the resulting lipid nanodisc includes a membrane protein spanning across at least one half of the lipid bilayer from one hydrophilic face to the center of the hydrophobic edge. In some cases, the lipid includes a membrane protein such that the resulting lipid nanodisc includes a membrane protein spanning across the entire lipid bilayer from one hydrophilic face to the center of the hydrophobic edge at least once.

The contacting step can include admixing the lipid and the copolymer in solution. An aqueous solution of copolymer can be prepared prior to contacting the copolymer with the lipid. A lipid dispersion can be prepared prior to contacting the copolymer with the lipid. The contacting step can includes admixing the polymer solution and the lipid suspension. The solutions and suspensions of the disclosure can be substantially free of a detergent. As used herein, "substantially free" means that the solution and/or suspension does not contain significant amounts of a purposefully added detergent. Thus, incidental or background quantity of detergents (e.g., less than about 100 ppb) may be present in the solution and/or suspension and be within the scope of the disclosure.

The contacting step can optionally further include a buffer to regulate the pH of the solution. Without intending to be bound by theory it is believed that in some embodiments, the pH of the solution can affect the charge of the copolymer, thus ultimately affecting solubility of the copolymer and stability of the resulting nanodiscs. The contacting step can be carried out at any suitable pH in which the copolymer is soluble, for example, in a range of about 0 to about 14, about 1 to about 12, about 2 to about 11, or about 2.5 to about 10, for example, about 2.5, about 3, about 3.5, about 4, about 4.5, about 5, about 5.5, about 6, about 6.5, about 7, about 7.5, about 8, about 8.5, about 9, about 9.5, or about 10.

In some embodiments, the copolymer can comprise a monomer that is zwitterionic under some pH conditions and positively or negatively charged under other pH conditions. Without intending to be bound by theory, it is believed that the presence of zwitterionic monomers in the copolymer chain inhibits the formation of nanodiscs due to the formation of hypercoils in the polymer chain from intramolecular charge-charge interactions. However, when the pH of the solution is modified such that the zwitterionic molecule becomes positively charged (i.e., acidic conditions) or when the pH of the solution is modified such that the zwitterionic monomer becomes negatively charged (i.e., basic conditions), the chains do not coil and stable nanodiscs can form. Thus, in some embodiments, the copolymer comprises a zwitterionic monomer and the pH of the contacting step is in a range of about 1 to about 5, about 1 to about 4, about 2 to about 4, about 3 to about 4, or about 3.5, or about 7 to about 14, about 7 to about 13, about 8 to about 12, about 8 to about 11, about 8 to about 10, about 8 to about 9, or about 8.5.

In some embodiments, the copolymer comprises a monomer that is positively charged under some pH conditions and neutral under other pH conditions. In some embodiments, the copolymer comprises a monomer that is negatively charged under some pH conditions and neutral under other pH conditions. Without intending to be bound by theory, it is believed that a positively or negatively charged monomer can increase the hydrophilicity (and solubility) of the hydrophilic portion of the copolymer relative to a neutral hydrophilic portion (e.g., ammonium cation demonstrates increased hydrophilicity and solubility relative to a neutral ammonia group). Thus, in some embodiments, the copolymer comprises a cationic monomer and the pH of the contacting step is in a range of about 1 to about 6, about 1 to about 5, about 2 to about 4, about 3 to about 4, or about 3.5. In some embodiments, the copolymer comprises an anionic monomer and the pH of the contacting step is in a range of about 8 to about 14, about 8 to about 13, about 8 to about 12, about 8 to about 11, about 8 to about 10, about 8 to about 9, or about 8.5.

The weight ratio of the lipid and the copolymer of the disclosure provided in the methods of the disclosure is not particularly limiting. The lipid and the copolymer can be provided in a ratio of about 3:1 to about 1:3 by weight, for example, a weight ratio of about 4:1 to about 1:4, about 3:1 to about 1:3, about 2:1 to about 1:2, or about 1:1. In some cases, the lipid and the copolymer are provided in a ratio in a range of about 1:1 to about 1:3, by weight. In some cases, the lipid and the copolymer are provided in a ratio in a range of about 4:1 to about 1:1.5, or about 3:1 to about 1:1, by weight. In general, as the weight of the copolymer is increased relative to the weight of the lipid, the maximum diameter of the resulting nanodiscs decrease. In some embodiments, there is an asymptotic value for the relative amount of the copolymer above which there is no further substantial decrease in the size/diameter of the nanodisc. For example, for the ethanolamine-modified styrene/maleic anhydride copolymer illustrated in the examples below, when the copolymer is provided in excess of 3 times the weight of the lipid (e.g., a 1:4, 1:5, or 1:6 lipid:copolymer weight ratio), the decrease in the maximum diameter of the resulting nanodiscs is negligible relative to the nanodiscs prepared from a 1:3 lipid:copolymer weight ratio.

The formation of the polymer-based lipid nanodiscs of the disclosure can be confirmed and characterized using a number of well-known techniques such as static light scattering (SLS), dynamic light scattering (DLS), size-exclusion chromatography (SEC), Fourier-transform infrared spectroscopy (FT-IR), solid-state nuclear magnetic resonance (ssNMR) and transmission electron microscopy (TEM). Advantageously, when the nanodiscs are less than or equal to about 40 nm, the structure of the nanodiscs can be determined based on solution NMR techniques and when the nanodiscs are greater than about 40 nm, the nanodiscs can be magnetically-aligned which is advantageous for solid-state NMR studies.

Method of Characterizing Membrane Proteins

The disclosure further provides a method of characterizing a membrane protein, the method including contacting a lipid nanodisc of the disclosure with a membrane protein to form a membrane protein-nanodisc including the membrane protein spanning across the lipid bilayer from one hydrophilic face to the center of the hydrophobic edge of the lipid nanodisc and characterizing the lipid nanodisc including the membrane protein. In some cases, the membrane protein spans across the entire lipid bilayer from the first hydrophilic face to the second hydrophilic face more than once. The membrane protein can be any membrane protein disclosed herein.

In some cases, the contact includes admixing the lipid nanodisc and membrane protein in solution. In some cases, the solution is substantially free of detergent.

Characterization can include at least one of a structural characterization of the membrane protein or a functional characterization of the membrane protein. Suitable membrane protein characterization methods include solution and solid state nuclear magnetic resonance (NMR), circular dichroism, electron paramagnetic resonance (EPR), Fourier transform infrared spectroscopy (FTIR), resonance Raman spectroscopy, ultraviolet-visible spectroscopy (UV/vis), cryo-electron microscopy (cryo-EM), surface plasmon Raman spectroscopy, sum frequency generation (SFG), fluorescence, including single molecule fluorescence and coherent anti-Stokes Raman (CARS), small angle x-ray scattering (SAXS), scanning electron microscopy (SEM), atomic force microscopy (AFM) and enzymatic assays Membrane protein structure and dynamics can be characterized using NMR techniques. For example, membrane protein-nanodiscs having a diameter of about 40 nm or less can be characterized using solution NMR and membrane protein-nanodiscs having a diameter greater than about 40 nm can be characterized using solid state NMR. Advantageously, the nanodiscs of the disclosure can include additional features for enhancing characterization by NMR, for example, the nanodisc may be characterized in that when a magnetic field is applied, the nanodisc aligns with the magnetic field and the nanodisc optionally includes a chelating group having a metal ion bound thereto as part of the pendant hydrophilic group which allows paramagnetic resonance characterization.

Magnetically aligned nanodiscs provide a novel membrane mimetic environment for the structural investigation of several membrane proteins by measuring $^1H$-$^{15}N$ heteronuclear dipolar couplings. One of the most popular approaches to measure heteronuclear dipolar couplings in ssNMR is the 2D separation of heteronuclear dipolar interactions according to chemical shifts. This class of experiments is known as Separated Local Field (SLF) spectroscopy. Polarization Inversion and Spin Exchange at Magic Angle (PISEMA) is a well-known and useful NMR technique for structural studies of a variety of biological systems.

The polymer-based lipid nanodiscs of the disclosure can be advantageous for one or more applications including, reconstitution of membrane proteins, purification of membrane proteins or peptides, drug deliver, and controlling the aggregation of amyloid peptides or proteins.

The above described aspects and embodiments can be better understood in light of the following examples, which are merely intended to be illustrative and are not meant to limit the scope in any way.

EXAMPLES

Example 1: Preparation of Styrene/Maleic Anhydride Copolymers Modified with Ethanolamine (SMA-EA Modified styrene/maleic anhydride copolymers were prepared according to the following reaction scheme:

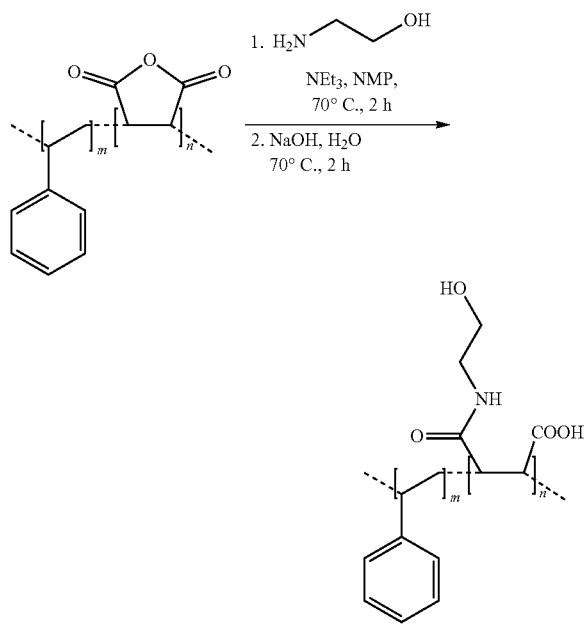

In particular, a 100 mg/mL solution of Poly(styrene-co-maleic anhydride), cumene terminated (SMA), with a 1.3:1 mole ratio of styrene:maleic anhydride and average Mn=1600 g/mol was prepared in 50 ml by dissolving 1 g of SMA in 10 mL of anhydrous N-Methyl-2-Pyrrolidone (NMP). To this solution, an excess of 10 ml of 2-Aminoethanol was added. A total of 700 µL of $Et_3N$ was added to the reaction, followed by incubation at 70° C. for 2 hours, after which the polymer was precipitated by the addition of 0.1 M HCl. The resulting ethanolamine modified polymer (SMA-EA) was washed with HCl several times and separated by centrifugation, followed by several cycles of washing the pellet in 600 µM acetic acid and centrifugation, to remove traces of NMP and 2-Aminoethanol. Finally, the polymer was lyophilized and stored at room temperature until use.

To hydrolyze any unreacted anhydride in the SMA-EA copolymer, 10 mg/mL suspensions of SMA-EA were heated in 1 M NaOH at 70° C. for 2 hours. Then the polymer was extracted by precipitation by the addition of 1 M HCl. The resulting precipitate was washed several times with water and lyophilized to give a white powder of SMA-EA in a quantitative yield.

The resulting SMA-EA polymer was characterized by FT-IR and ssNMR. The SMA-EA contained the pendant alkylhydroxy group and carboxylic group resulting from the ring-opening of the maleic anhydride. In the SMA-EA spectrum, there was a characteristic broad band in the region 3000-3600 $cm^{-1}$ and centered around 3500 $cm^{-1}$ that corresponded to a combination of the stretching bands of —O—H in the carboxylic group and in the alcoholic group. The same spectrum showed a band at 1668 $cm^{-1}$ shifted to lower wavenumber compared to the starting SMA copolymer, suggesting the formation of amides and complete opening of anhydride ring of SMA.

The SMA-EA was further characterized by $^{13}C$ Cross-Polarization Magic Angle Spinning ssNMR spectroscopy ($^{13}C$ CP-MAS ssNMR). The comparison between SMA and SMA-EA spectra, showed peaks at 41, 60 and 128 ppm corresponding to aliphatic and aromatic carbons respectively. A peak around 172 ppm was assigned to the carbonyl carbon in maleic anhydride which was shifted 5.7 ppm lower field in SMA-EA, suggesting the formation of amides in the SMA-EA compound.

Thus, Example 1 demonstrates the preparation of a copolymer according to the disclosure.

Example 2: Preparation of Polymer-Based Lipid Nanodiscs

A 20 mg/ml stock solution of the SMA-EA copolymer of Example 1 was prepared. To the stock solution was added 2 mL of a 10 mg/mL solution of 1,2-dimyristoyl-sn-glycero-3-phosphocholine (DMPC) to provide a 1:1 weight ratio of lipid to polymer in 10 mM HEPES buffer solution. The formation of lipid nanodiscs was followed using static light scattering (SLS) using a FLUORMAX 4 from HORIBA SCIENTIFIC using a 1 ml cuvette (or equivalent). The resulting transparent solution was also analyzed using dynamic light scattering (DLS) which showed a plurality of nanodiscs. The maximum size of the nanodisc achieved using the copolymer of Example 1 at a 1:1 lipid:polymer ratio was about 60 nm. DLS was performed using WYATT TECHNOLOGY DYNAPRO NANOSTAR using a 1 microliter quartz micro cuvette (or equivalent).

Additional nanodiscs were formed as described above using lipid:polymer weight ratios of 1:2 and 1:3. The maximum size of the nanodisc formed using the lipid:polymer weight ratios of 1:2 and 1:3 were about 24 nm and about 10 nm, respectively.

As shown in FIG. 2 panel A, the maximum size of the nanodiscs varied based on the weight ratio of lipid:polymer, as illustrated as the mass distribution as a function of hydrodynamic radius. FIG. 2 panel B shows the TEM micrograph of the nanodiscs obtained by mixing a 1:1 w/w ratio DMPC:SMA-EA and FIG. 2 panel C shows the TEM micrograph of the nanodiscs obtained by mixing a 1:3 w/w ratio of DMPC:SMA-EA. Thus, Example 2 demonstrates formation of nanodiscs according to the disclosure and the size dependency on the lipid:polymer ratios.

Example 3: Mechanism of Nanodisc Formation

The mechanism of the formation of nanodiscs was investigated. To study the mechanism of nanodisc formation, three separate samples were prepared using same stock solutions and the same conditions. Sample preparation consisted of mixing of 10 mg/ml DMPC solution with SMA-EA in a 1:1 w/w lipid to polymer ratio. The first sample was flash frozen with liquid nitrogen (LN) immediately, whilst the other two samples were vortexed for 1 and 3 minutes respectively. These were lyophilized overnight and the resulting powder samples were analyzed using FT-IR and ssNMR. The FT-IR spectrum of the lipid-polymer mixture, frozen after 3 minutes, exhibited an increase in the 1592 $cm^{-1}$ peak compared to the lipid-polymer mixture frozen at time zero. This corresponds to the aromatic double bond bending (C=C bending), and suggests an increased interaction between the aromatic styrene group of the copolymer and the lipid chain of the lipid bilayer. The peak at 1240 $cm^{-1}$ is due to the lipid phosphate groups shifting to a higher wavenumber and suggests the polymer insertion into bilayer with the time. $^1D$ $^{31}P$ MAS NMR spectra of the polymer lipid mixture showed a chemical shifts between time point 0 minutes and time point 3 minutes, indicating that the change in the chemical environment of phosphorous in the mechanism of the interaction of the SMA-EA polymer with the DMPC lipid head groups.

The nanodisc formation mechanism was also studied using ultrafast $^1H/^1H$ homonuclear correlation radio frequency driven recoupling (RFDR) NMR (MAS@60 kHz) technique. The 2D $^1H/^1H$ RFDR spectrum suggested that the polymer hydrophilic part interacts with the surface of the bilayer, after that the hydrophilic portion was inserted into the bilayer and a nanodisc formed. Formation of the nanodisc was determined from the cross peaks between styrene aromatic protons (7.1 ppm) with the DMPC hydrophobic chain at 3-min, which are absent in the 0-min sample.

One dimensional $^{31}P$ NMR spectra of polymer nanodiscs and macrodiscs recorded at 35° C. showed the magnetic alignment of the polymer macrodiscs (~50 nm in diameter). At room temperature, macrodiscs (~50 nm in diameter) showed a characteristic chemical shift anisotropy (CSA) powder pattern indicating the sum of all orientations of the phosphate group in DMPC lipids relative to the external magnetic field. At 35° C., the $^{31}P$ spectrum of the macrodiscs showed one single peak at a chemical shift of −17.91 ppm with narrow line width (~250 Hz), whereas the nanodiscs showed a single peak at a chemical shift of −2.1 ppm. This frequency shift is a crucial evidence that the lipids in macrodiscs align with their normal perpendicular to the direction of the magnetic field since the aligned peak appears as a single peak at the perpendicular edge of powder pattern. The narrow line widths in the $^{31}P$ NMR spectra demonstrated that the lipids are arranged homogeneously and that the macrodiscs are uniformly aligned in the magnetic field. 1D $^{14}N$ NMR experiments were also employed to get the $^{14}N$ quadrupolar splitting of these magnetically aligned nanodiscs. The electric field gradient around the $^{14}N$ nucleus was considerably reduced due to the near-tetrahedral symmetry of the choline groups of DMPC molecules and hence the quadrupole coupling was also reduced.

Thus, Example 3 demonstrates formation of nanodiscs of the disclosure by interaction between the aromatic styrene group of the copolymer and the lipid chain of the lipid bilayer resulting in insertion of the aromatic styrene group into bilayer over time. The hydrophilic part of the polymer then interacts with the surface of the bilayer to insert the hydrophilic portion into the bilayer and form a nanodisc.

Example 4: Characterization of Membrane Proteins 20 mg of SMA-EA was added to 20 mg of DMPC (10 mg/ml in 10 mM HEPES buffer), and incubated for 30 min. The resulting mixture was subjected to 3 freeze/heat cycles between liquid nitrogen (~−196° C.) and 50° C. Protein corresponding to 1 mmol U-$^{15}$N-labeled Cytb5 was added to the macrodisc solution and incubated for 2 hrs, followed by concentrating the total volume to 200 μl to provide a highly viscous cytochrome-b5 reconstituted macrodiscs solution. The degree of sample alignment was measured using $^{31}P$ NMR.

2D $^1H$-$^{15}N$ PISEMA experiments were employed to understand the helicity pattern in the transmembrane domain (TM) region of the U-15N-labeled Cytb5 protein. This technique correlates $^{15}N$ chemical shifts with $^1H$-$^{15}N$ dipolar couplings and the 2D spectrum provides indices of secondary structure and topology of membrane peptides embedded in lipid bilayers.

The distinct geometry of the transmembrane α-helix of Cytb5 gave rise to a characteristic 'wheel-like' pattern of resonances reflecting helical wheel projections of residues from transmembrane helices. This helical wheel pattern has been referred to as PISA (polarity index slant angle) wheel. The center of the PISA wheel uniquely reflects the specific tilt or slant angle (τ), of the helical axis with respect to the bilayer normal. PISA wheel patterns can be obtained by calculating $^{15}N$ chemical shift and the $^1H$-$^{15}N$ dipolar coupling values for different tilt angles of a helix. MATLAB simulations were performed to determine the tilt angle of the transmembrane helix in Cytb5. The helical wheel pattern analysis revealed that the Cytb5 helix is tilted by 14.5±3° away from the lipid bilayer normal. The heteronuclear correlation of the amide groups with the attached protons in the back bone of the soluble domain was determined using 2D $^1H$-$^{15}N$ TROSY-HSQC (Transverse Relaxation Optimized SpectroscopY Heteronuclear Single Quantum Correlation). The 2D spectrum showed well-dispersed contours and the protein was well folded in structure. The 2D spectrum was well-consistent with the data already reported in the literature for the Cytb5.

Example 5: Preparation of Zwitterionic Styrene/Maleic Anhydride Copolymers Modified with Ethylenediamine (SMA-ED Zwitterionic, modified styrene/maleic anhydride copolymers were prepared according to the following reaction scheme:

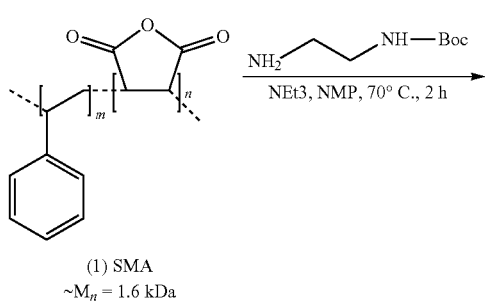

(1) SMA
~$M_n$ = 1.6 kDa

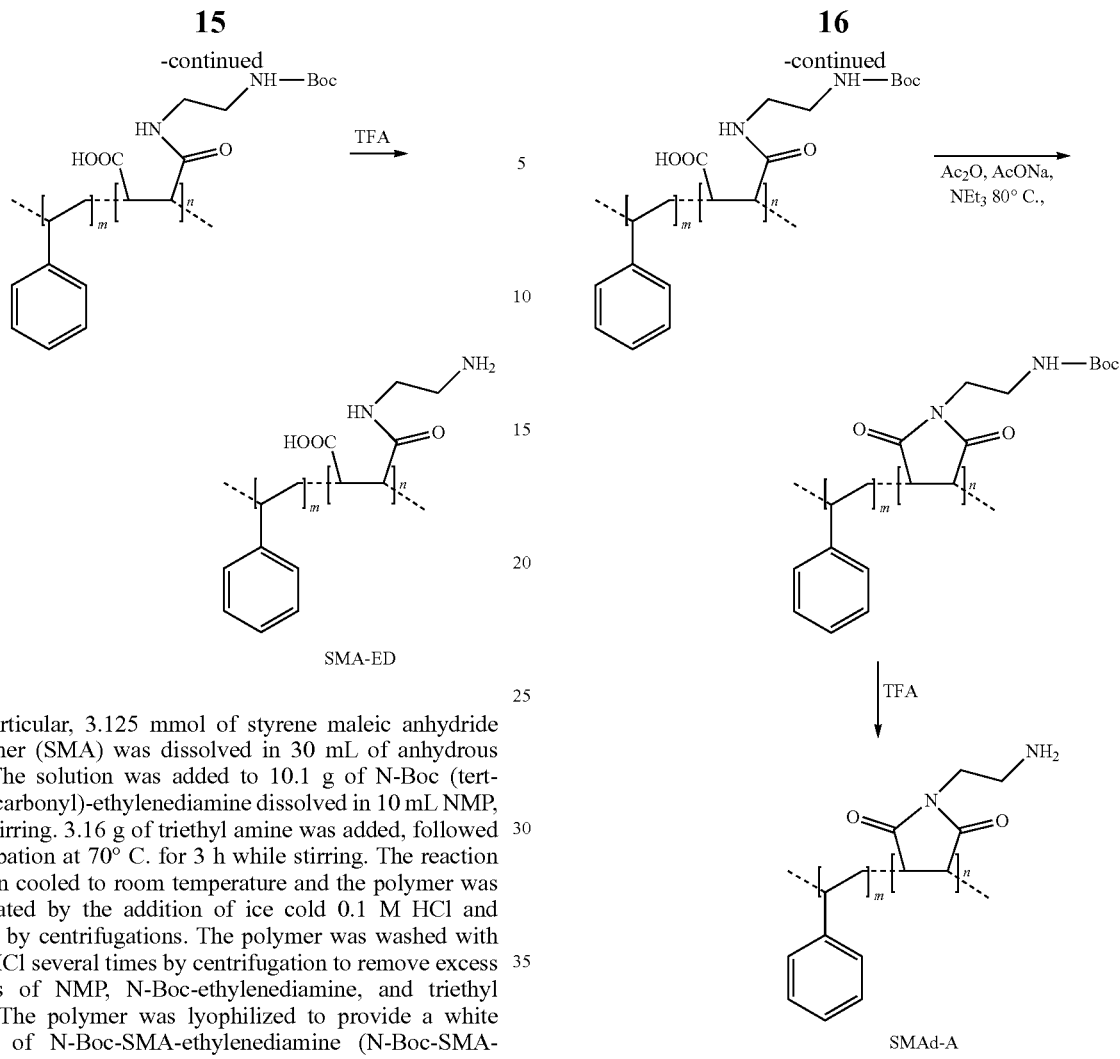

SMA-ED

In particular, 3.125 mmol of styrene maleic anhydride copolymer (SMA) was dissolved in 30 mL of anhydrous NMP. The solution was added to 10.1 g of N-Boc (tert-Butoxycarbonyl)-ethylenediamine dissolved in 10 mL NMP, while stirring. 3.16 g of triethyl amine was added, followed by incubation at 70° C. for 3 h while stirring. The reaction was then cooled to room temperature and the polymer was precipitated by the addition of ice cold 0.1 M HCl and pelleted by centrifugations. The polymer was washed with 0.1 M HCl several times by centrifugation to remove excess amounts of NMP, N-Boc-ethylenediamine, and triethyl amine. The polymer was lyophilized to provide a white powder of N-Boc-SMA-ethylenediamine (N-Boc-SMA-ED).

2 g of N-Boc-SMA-ED was dissolved in 40 mL of trifluoroacetic acid (TFA) and 2 mL of water and was stirred for 3 h. The reaction solution was then precipitated in cold ether and then washed by centrifugation and cold ether to SMA-ethylenediamine (SMA-ED). Thus, Example 5 shows the preparation of a copolymer according to the disclosure.

Example 6: Preparation of Styrene/Maleic Anhydride Copolymers Modified with Ethylenediamine (SMAd-A Ethylenediamine modified styrene maleic anhydride copolymers were prepared according to the following scheme:

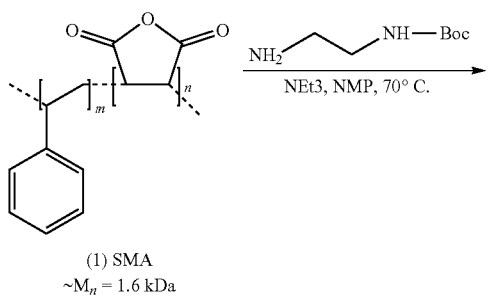

(1) SMA
~$M_n$ = 1.6 kDa

SMAd-A

In particular, 0.32 mmol of N-Boc SMA-ED as prepared in Example 5 was added to 20 mL acetic anhydride. 330 mg of sodium acetate and 100 mg of triethylamine were added and stirred to make a homogenous mixture. The reaction mixture was then heated to 80° C. and stirred overnight. The mixture was then precipitated in cold water and washed via centrifugation with cold water and freeze-dried to provide N-Boc-SMAd-A.

470 mg of N-Boc-SMAd-A was dissolved in 40 mL TFA and 2 mL of water followed by stirring for 3 h. The reaction solution was then precipitated in cold ether and then washed by centrifugation with cold ether. The resulting SMAd-A copolymer was then dried under vacuum. Thus, Example 6 shows preparation of a copolymer according to the disclosure.

Example 7: Preparation of Polymer-Based Lipid Nanodiscs

Nanodiscs were formed by the addition of 100 μL DMPC (10 mg/mL) and 100 μL of SMA-ED (according to Example 5) or SMAd-A (according to Example 6) (10 mg/mL) in a 1.5 mL tube and diluted to 1 mL using water, 10 mM citric acid buffer pH 3.5, or 10 mM HEPES buffer pH 8. The formation of lipid nanodiscs was followed using static light scattering (SLS) using a FLUORMAX 4 from HORIBA SCIENTIFIC using a 2 ml cuvette (or equivalent). 500 μL of nanodiscs were dispensed into a 2 mL cuvette under stirring. The solution was then diluted to 2 mL with citric acid buffer or HEPES buffer, as required. pH titrations were performed using 1 M HCl and NaOH. Metal ion titrations were performed using 5 M $MgCl_2$, 5 M NaCl, and 2.2 M $CaCl_2$. The excitation and emission wavelengths were all set at 400 and 404 nm, respectively. The slit was set to 2 nm.

For the nanodiscs prepared in water, a significant decrease in SLS intensity was demonstrated after the addition of polymer, suggesting that both SMA-ED (FIG. 3A) and SMAd-A (FIG. 3B) can solubilize DMPC multilamellar vesicle (MLVs). The DLS profiles of the nanodiscs demonstrate the dependence of nanodisc size on the lipid:polymer ratio (FIG. 3C, D) and the nanodiscs were confirmed by TEM (FIG. 3E, F).

Figure 4C:
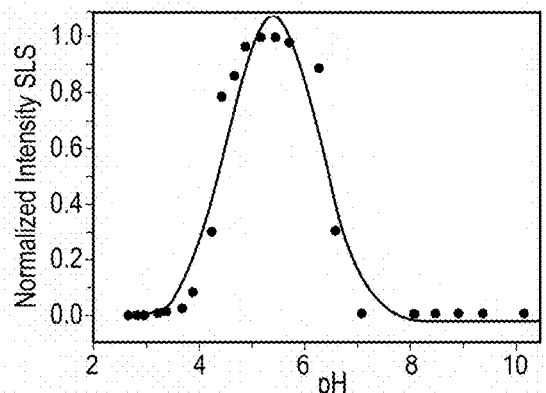
Figure 4D:
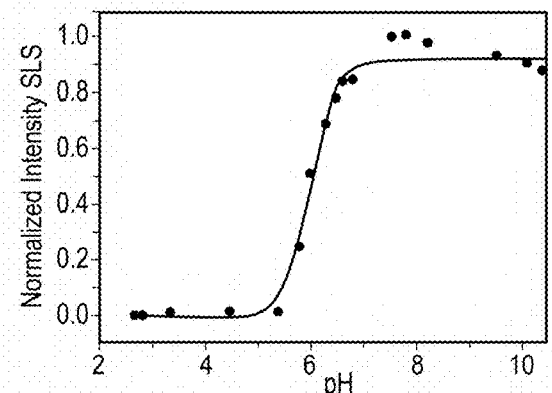
Figure 4E:
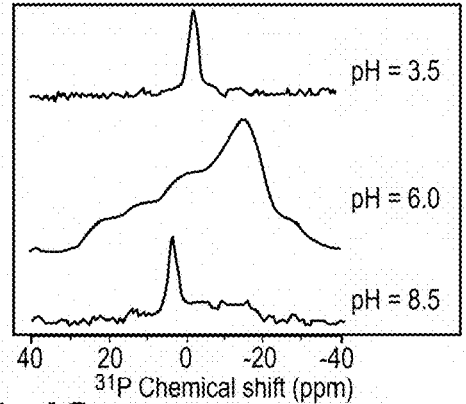
Figure 4F:
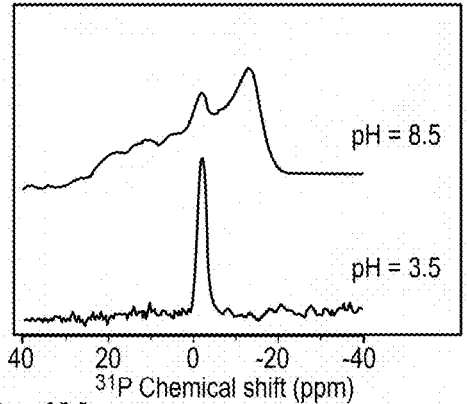
Figure 4G:
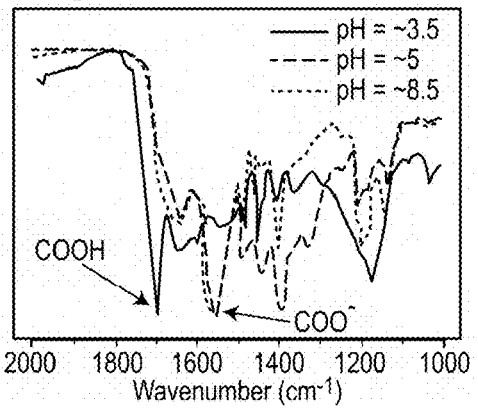
Figure 4H:
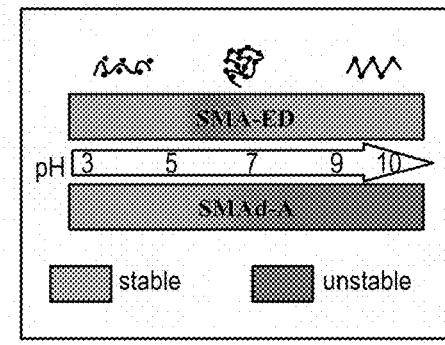

When the preparation of the nanodiscs was performed at pH 7.4 in phosphate buffer, SMA-ED showed nanodisc formation whereas SMAd-A did not form nanodiscs, suggesting a pH dependent nanodisc formation. Experimental results obtained under different pH conditions were used to analyze the stability of nanodisc formed by both polymers. SMA-ED nanodiscs showed increased light scattering, and visible precipitate formation between pH 5 and 7 (FIG. 4A). This scattering suggests that SMA-ED is stable under all pH conditions except between 5 and 7. This is because the polymer is zwitterionic and forms hypercoils due to intramolecular charge-charge interactions, as confirmed by SLS and FT-IR. SLS profiles for pH titrations of polymer alone are similar to that of the nanodiscs (FIG. 4C), showing SMA-ED polymer aggregates and lowers in solubility due to hypercoiling. FT-IR showed the presence of carboxylate at pH 5, supporting the presence of the zwitterionic form of the SMA-ED polymer in the 5-7 pH range (FIGS. 4G and H). NMR experiments at pH 3.5 and 8.5 suggest the formation of nanodiscs that tumble rapidly on the NMR time scale (FIG. 4E). In contrast, the pattern observed at pH 6 suggests the inability of the polymer to form nanodiscs.

The SLS intensity of SMAd-A nanodiscs was stable for pH<6. A steep increase in intensity and the formation of a visible precipitate was observed for pH>6. These results suggest that SMAd-A polymer nanodiscs are stable under acidic pH. A similar profile was observed for the SMAd-A polymer alone (FIG. 4D). The NMR spectra indicated the presence of a nanodisc under acidic pH, and no nanodisc formation as the pH increased above 6 (FIG. 4F), consistent with the observations of the SLS experiments. The SMAd-A polymer is positively charged under acidic conditions, soluble in water, and forms lipid nanodiscs. For pH>6, the solubility of the polymer is decreased due to deprotonation of the ammonium cation leading to polymer precipitation.

The stabilities of SMA-ED and SMAd-A in the presence of different divalent cations were examined using SLS. Both the SMA-ED and SMAd-A based nanodiscs were stable in the presence of a monovalent sale (NaCl), at various concentrations (10-200 mM). Both SMA-ED and SMAd-A nanodiscs were also found to be tolerant to $Ca^{2+}$ and $Mg^{2+}$ for all the tested concentrations (10 to 200 mM of $MgCl_2$ and $CaCl_2$). However, at pH 8.5 soluble nanodiscs (SMA-ED) had no tolerance to $Ca^{2+}$ or $Mg^{2+}$ due to the presence of $COO^-$ groups that can interact with the metal ions.

Example 8: Preparation of Styrene/Maleic Anhydride Copolymers Modified with (2-Aminoethyl)Trimethylammonium (SMA-QA (2-aminoethyl)trimethylammonium modified styrene maleic anhydride copolymers were prepared according to the following scheme:

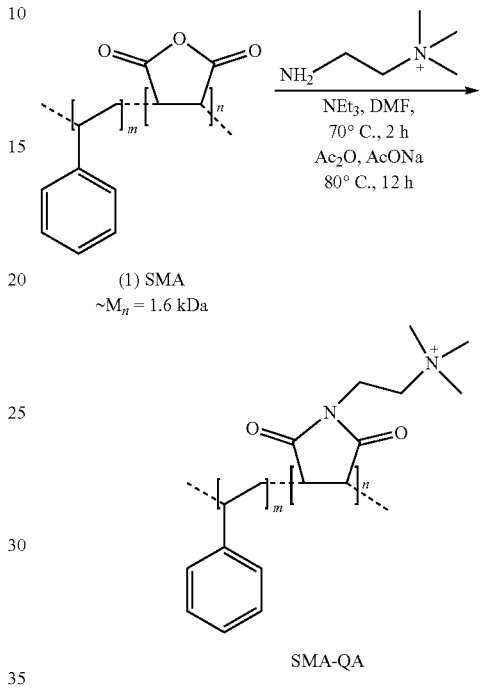

1 g of SMA (about 1600 g/mol) was dissolved in 30 ml of anhydrous dimethylformamide (DMF) dried over molecular sieves. 1.3 g of (2-aminoethyl)trimethylammonium chloride hydrochloride was then added to the solution and to this mixture 5 ml of trimethylamine was added resulting in the solution turning dark yellow. The reaction mixture was then stirred at 100° C. for 12 h. The solution was cooled to room temperature and precipitated with diethyl ether. The precipitate was washed 3 times with diethyl ether and dried under vacuum. The dried intermediate was then added to 30 ml acetic anhydride. 660 mg of sodium acetate and 200 mg of triethyl amine were then added. The reaction mixture was heated at 100° C. overnight and precipitated in ether. The precipitate was washed 3 times with ether and dried under vacuum. The product was then dissolved in water and passed through a SEPHADEX LH-20 column. The product was collect and lyophilized to provide a brown powder. The resulting SMA-QA was characterized by FT-IR and NMR experiments. Thus, Example 8 demonstrates preparation of a copolymer of the disclosure.

Example 9: Preparation of Polymer-Based Lipid Nanodiscs with Sma-Qa

Nanodiscs of differing sizes were prepared using DMPC (10 mg/ml) in 20 mM sodium phosphate buffer containing 50 mM NaCl at pH 7.4. 10 mg/ml of polymer stock solutions were made in the same buffer solution. The required amount of polymer solution to provide a lipid:SMA-QA ratio of 1:0.25, 1:0.5, 1:1.0, or 1:1.5, was added to the DMPC mixture and incubated for 4 h at 35° C. The samples made using DMPC:SMA-QA weight ratios of 1:0.25 and 1:0.5 were prepared using three freeze thaw cycles alternating between liquid nitrogen temperature and 35° C. After the freeze thaw cycles the samples were further incubated at 35° C. for 4 h.

Figure 5:
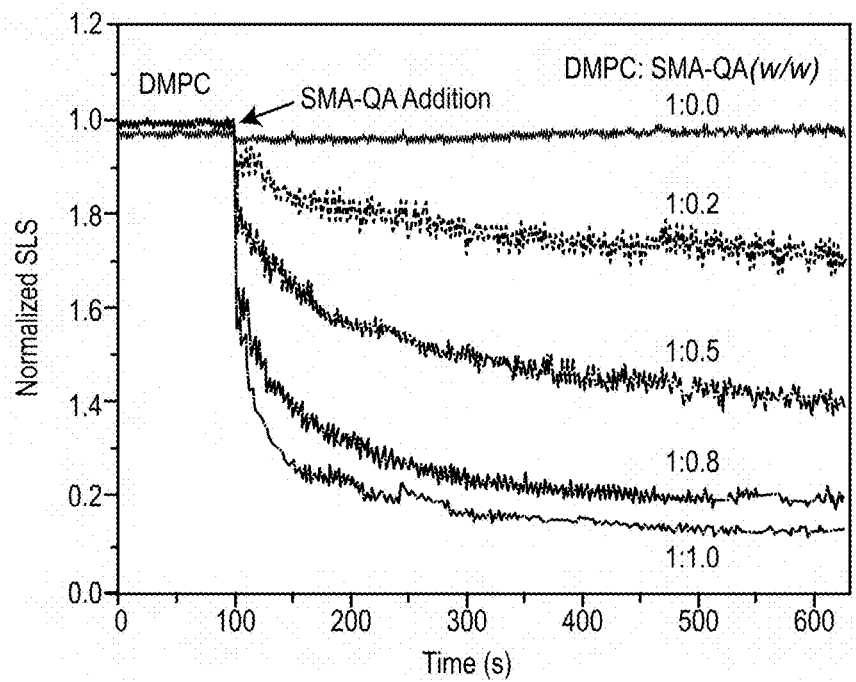
FIG. 5 shows the SLS profiles showing the kinetics of DMPC MLVs solubilization by SMA-QA.
Figure 6:
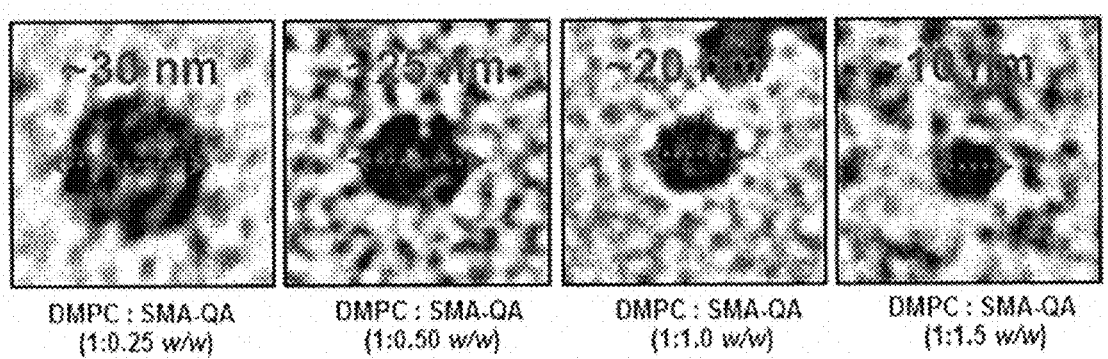
FIG. 6 shows TEM images of DMPC-SMA-QA nanodiscs formed with the indicated lipid to polymer ratio.

FIG. 5 shows the SLS profiles of DMPC MLVs for different lipid to polymer weight ratios. The large intense scattering dramatically decreased upon the addition of SMA-QA polymer, demonstrating the solubilization of large DMPC MLVs into small size polymer-lipid nanodiscs. The rate of solubilization of MLVs was accelerated by the increase of the amount of SMA-QA. DLS profiles showed the hydrodynamic radii of the nanodiscs were dependent on the ratio of DMPC to SMA-QA. TEM images of the nanodiscs confirmed the presence of disc shaped, monodispersed particles with remarkable highly circular shape (FIG. 6).

The $^{31}$P spectrum of DMPC:SMA-QA (1:0.25 w/w) shows a single narrow peak ~16 ppm demonstrating the magnetic-alignment of polymer nanodiscs with the bilayer normal perpendicular to the magnetic field direction. Due to the large size (~30 nm diameter), the slow tumbling of nanodiscs allows for the magnetic alignment in the presence of an external magnetic field. On the other hand, a narrow peak was observed at the isotropic chemical shift frequency (~-2 ppm) for small nanodiscs (~10 nm diameter) demonstrating their fast tumbling in the NMR time scale.

Figure 7:
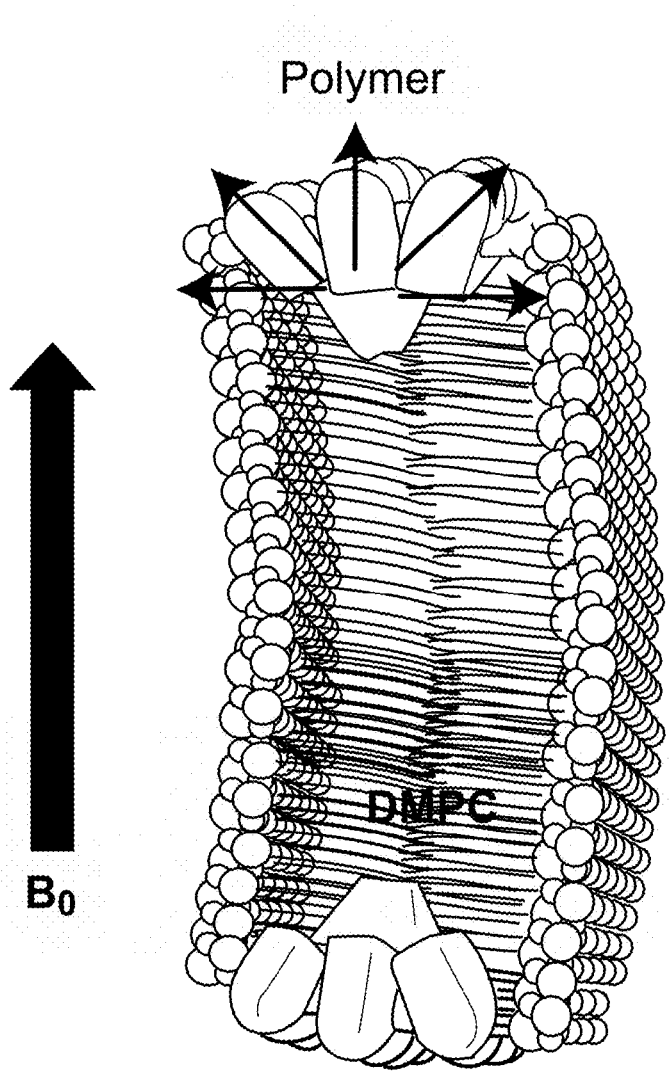
FIG. 7 shows a schematic of a nanodisc illustrating the orientations of the lipid headgroup and polymer in magnetically-aligned nanodiscs.

The $^{14}$N NMR spectra of SMA-QA nanodiscs (~30 nm diameter) containing phosphatidyl choline head group containing lipids (like DMPC or POPC) show a quadrupole coupling spectrum indicating magnetic alignment of nanodiscs. The nanodiscs are unaligned when the lipids are in the gel phase, but they start to align in the magnetic field when the temperature is increased above the main phase transition temperature of the lipids. A narrow line (isotropic) is observed for an unaligned sample, while a doublet is observed for an aligned lipid bilayer. The magnitude of the observed quadrupolar coupling indicates the nanodiscs are aligned in the magnetic field with the lipid bilayer normal to the direction of the magnetic field, for example as illustrated in FIG. 7. These results further confirm the magnetic alignment of large size nanodiscs indicated by $^{31}$P NMR spectra.

The stability of the SMA-QA nanodiscs against pH and metal ion concentration was examined using SLS measurements. The SLS profiles of the nanodiscs DMPC:SMA-QA (1:1 w/w) showed no change in the scattering intensity over a wide range of pH (from 2.5 to 10) and in the presence of metal ion concentrations up to 200 mM.

Thus, Example 9 demonstrates polymer based lipid nanodiscs of the disclosure advantageously demonstrating at least one of pH stability, ion stability, and/or magnetic alignment properties.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer, component, or step or groups of integers, components, or steps but not to the exclusion of any other integer, component, or step or groups of integers, components, or steps.

Throughout the specification where compositions are described as including components or materials, it is contemplated that the composition can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

All patents, publications and references cited herein are hereby fully incorporated by reference. In case of conflict between the present disclosure and incorporated patents, publications and references, the present disclosure should control.

What is claimed:

1. A lipid nanodisc comprising:
   a lipid bilayer comprising two opposing hydrophilic faces and a hydrophobic edge between the hydrophilic faces; and
   a copolymer encircling the hydrophobic edge of the lipid bilayer, the copolymer comprising
      a first monomeric unit comprising a pendant aromatic group, and
      a second monomeric unit comprising a pendant hydrophilic group,
      wherein the first monomeric unit and the second monomeric unit are present in the copolymer in a molar ratio ranging from 1:1 to 3:1 for the first monomeric unit:the second monomeric unit, wherein the copolymer is not zwitterionic.

2. The lipid nanodisc of claim 1, wherein the first monomeric unit comprises a styrene monomer unit.

3. The lipid nanodisc of claim 1, wherein the second monomeric unit comprises a modified maleic anhydride or modified maleic acid monomer unit.

4. The lipid nanodisc of claim 1, wherein the pendant hydrophilic group comprises at least one of hydroxyl, amino, carboxylic acid, carboxylate, phosphate, phosphonate, carboxylic ether, carboxylic ester, phosphate ester, amide, phosphonamide, or salts of the foregoing.

5. The lipid nanodisc of claim 1, wherein the pendant hydrophilic group comprises at least one of a fluorescent group and a chelating group further comprising a metal ion bound thereto.

6. The lipid nanodisc of claim 1, wherein the copolymer has a number-average molecular weight ranging from 1 kDa to 6 kDa.

7. The lipid nanodisc of claim 1, wherein the lipid comprises at least one of phosphatidylethanolamines, phosphatidylcholines, phosphatidylglycerols, phosphatidylserines, cholesterols, sphingomyelin, gangliosides, lipopolysaccharides, phosphatidylinositols, and derivatives of the foregoing.

8. The lipid nanodisc of claim 1, wherein the nanodisc has a diameter in a range of about 6 nm to about 100 nm.

9. The lipid nanodisc of claim 1, further comprising a membrane protein spanning across the lipid bilayer from the first hydrophilic face to the second hydrophilic face.

10. The lipid nanodisc of claim 1, wherein the molar ratio of the pendant hydrophilic group to the second monomer unit in the copolymer is about 2:1 to 1:10.

11. A method of making a lipid nanodisc, the method comprising:
   contacting:
      a lipid; and
      a copolymer comprising
         a first monomeric unit comprising a pendant aromatic group, and a second monomeric unit comprising a pendant hydrophilic group, wherein the first monomeric unit and the second monomeric unit are present in the copolymer in a molar ratio ranging from 1:1 to 3:1 for the first monomeric unit:the second monomeric unit and the copolymer is not zwitterionic, to form a lipid nanodisc comprising a lipid bilayer comprising two opposing hydrophilic faces and a hydrophobic edge between the hydrophilic faces and the copolymer encircling the hydrophobic edge of the lipid bilayer.

12. The method of claim 11, further comprising preparing an aqueous solution of the copolymer prior to contacting the copolymer with the lipid.

13. The method of claim 11, further comprising preparing a lipid dispersion prior to contacting the copolymer with the lipid.

14. The method of claim 11, wherein the contacting comprises admixing the lipid and the copolymer in solution.

15. The method of claim 11, wherein the lipid and the copolymer are provided in a ratio of about 3:1 to about 1:3, by weight.

16. The method of claim 11, wherein the lipid comprises at least one of phosphatidylethanolamines, phosphatidylcholines, phosphatidylglycerols, phosphatidylserines, cholesterols, sphingomyelin, gangliosides, lipopolysaccharides, phosphatidylinositols, and derivatives of the foregoing.

17. A method of characterizing a membrane protein, the method comprising:

contacting the lipid nanodisc of claim 1 with a membrane protein to form a membrane protein-nanodisc comprising the membrane protein spanning across the lipid bilayer from the first hydrophilic face to the second hydrophilic face; and characterizing the lipid nanodisc comprising the membrane protein.

18. The method of claim 17, wherein characterizing comprises at least one of structural characterization and functional characterization, the characterization comprising performing at least one of solution nuclear magnetic resonance (NMR), solid state NMR, circular dichroism, electron paramagnetic resonance (EPR), Fourier transform infrared spectroscopy (FTIR), resonance Raman spectroscopy, ultraviolet-visible spectroscopy (UV/vis), cryo-electron microscopy (cryo-EM), surface plasmon Raman spectroscopy, sum frequency generation (SFG), fluorescence, small angle x-ray scattering (SAXS), scanning electron microscopy (SEM), atomic force microscopy (AFM), and an enzymatic assay.

19. The lipid nanodisc of claim 1, wherein the lipid nanodisc is prepared by contacting the lipid and the copolymer in a ratio of about 3:1 to about 1:1, by weight.

20. The lipid nanodisc of claim 1, wherein the nanodisc has a diameter in a range of about 10 nm to about 90 nm.

21. The lipid nanodisc of claim 1, wherein the copolymer has a number-average molecular weight ranging from 1 kDa to 3 kDa.

22. The lipid nanodisc of claim 10, wherein the molar ratio of the pendant hydrophilic group to the second monomer unit in the copolymer is about 2:1 to about 1:4.

23. The lipid nanodisc of claim 10, wherein the molar ratio of the pendant hydrophilic group to the second monomer unit in the copolymer is about 1:1.

* * * * *

UNITED STATES PATENT AND TRADEMARK OFFICE
CERTIFICATE OF CORRECTION

| | | |
|---|---|---|
| PATENT NO. | : 11,092,605 B2 | |
| APPLICATION NO. | : 16/198397 | |
| DATED | : August 17, 2021 | |
| INVENTOR(S) | : Ramamoorthy et al. | |

It is certified that error appears in the above-identified patent and that said Letters Patent is hereby corrected as shown below:

In the Claims

At Column 20, Line 20, "comprising" should be -- comprising: --.

At Column 20, Line 65, "comprising" should be -- comprising: --.

At Column 22, Line 10, "solid state" should be -- solid-state --.

Signed and Sealed this
Fifth Day of September, 2023

Katherine Kelly Vidal
*Director of the United States Patent and Trademark Office*